United States Patent
Howard, III et al.

[11] Patent Number: 6,128,527
[45] Date of Patent: Oct. 3, 2000

[54] APPARATUS AND METHOD OF ANALYZING ELECTRICAL BRAIN ACTIVITY

[75] Inventors: Matthew A. Howard, III, Iowa City; Charles Garell; Daniel Noh, both of Coralville, all of Iowa

[73] Assignee: University of Iowa Research Foundation, Iowa City, Iowa

[21] Appl. No.: 08/984,024

[22] Filed: Dec. 3, 1997

[51] Int. Cl.[7] .................................................. A61B 5/00
[52] U.S. Cl. .......................... 600/544; 600/545; 600/378
[58] Field of Search ................................ 600/544–545, 600/378; 128/920–925

[56] References Cited

U.S. PATENT DOCUMENTS

| | | | |
|---|---|---|---|
| 3,676,783 | 7/1972 | Kinbara et al. | 328/117 |
| 3,818,356 | 6/1974 | Kinbara et al. | 328/112 |
| 3,857,399 | 12/1974 | Zacouto | 128/419 |
| 4,052,991 | 10/1977 | Zacouto | 128/419 |
| 4,337,779 | 7/1982 | Spevak et al. | 128/691 |
| 4,399,512 | 8/1983 | Soma et al. | 364/487 |
| 4,421,122 | 12/1983 | Duffy | 600/544 |
| 4,552,154 | 11/1985 | Hartlaub | 128/702 |
| 4,653,500 | 3/1987 | Osaeda et al. | 128/639 |
| 4,753,246 | 6/1988 | Freeman | 600/544 |
| 4,768,519 | 9/1988 | Yamaguchi | 128/680 |
| 4,852,573 | 8/1989 | Kennedy | 600/544 |
| 4,867,171 | 9/1989 | Yamaguchi | 128/680 |
| 5,320,109 | 6/1994 | Chamoun et al. | 600/544 |
| 5,411,529 | 5/1995 | Hudrlik | 607/6 |
| 5,447,166 | 9/1995 | Gevins | 600/544 |
| 5,563,067 | 10/1996 | Sugihara et al. | 435/287 |
| 5,649,936 | 7/1997 | Real | 606/130 |
| 5,692,517 | 12/1997 | Junker | 600/545 |
| 5,817,106 | 10/1998 | Real | 606/130 |

FOREIGN PATENT DOCUMENTS

WO 95/21591   8/1995   WIPO .

OTHER PUBLICATIONS

P.C. Garell et al., "Introductory overview of research instruments for recording the electrical activity of neurons in the human brain;" Review of Scientific Instruments, 1998 American Institute of Physics, vol. 69, No. 12, Dec. 1998; pp. 4027–4037.

*Primary Examiner*—Max Hindenburg
*Assistant Examiner*—Michael Astorino
*Attorney, Agent, or Firm*—Fleshner & Kim, LLP

[57] ABSTRACT

An apparatus and method for mapping a patient's brain includes analyzing the waveform of electrical action potentials generated in the patient's brain to determine whether the waveforms match one or more predetermined waveforms. A system embodying the invention includes waveform discriminator circuitry capable of comparing the waveform of a sensed electrical action potential to predetermined waveforms. A system embodying the invention may also include a user interface for selecting a waveform and a transducer for generating a user recognizable signal when a waveform of a sensed electrical action potential matches a selected waveform.

42 Claims, 10 Drawing Sheets

APPARATUS AND METHOD OF ANALYZING ELECTRICAL BRAIN ACTIVITY

BACKGROUND OF THE INVENTION

1. Field of the Invention

The invention relates to methods and apparatus for sensing and analyzing electrical activity in a patient's brain. In particular, the invention relates to sensing an electrical action potential generated in a selected portion of a patient's brain and comparing a waveform of the electrical action potential to one or more predetermined waveforms.

2. Background of the Related Art

It is known that different regions of the brain are used to control different parts of the body and to process different sensory inputs. It is also known that when a human performs a certain function, such as moving an extremity or listening to a particular sound, a discrete region of the brain will generate electrical action potentials to accomplish that function. It is also known that direct electrical stimulation of a particular region of the brain can cause at least partial reproduction of the functions or sensory input normally associated with that region of the brain.

Determining which portions of a patient's brain are responsible for certain motor activities or certain sensory functions has become known as brain "mapping." After a patient's brain has been mapped, the brain can be electrically stimulated to restore lost functions.

For instance, it is possible to determine which portions of a patient's brain are responsible for processing particular sound frequencies. Once a neurosurgeon knows which portions of the patient's brain are responsible for processing each sound frequency, it is possible to electrically stimulate selected portions of the patient's brain to cause the patient to "hear" particular sounds. Thus, a patient whose hearing has been partially or permanently damaged can be made to hear again if an electrical prosthetic device is used to sense sounds and to electrically stimulate the brain to perceive those sounds.

Figure 1:
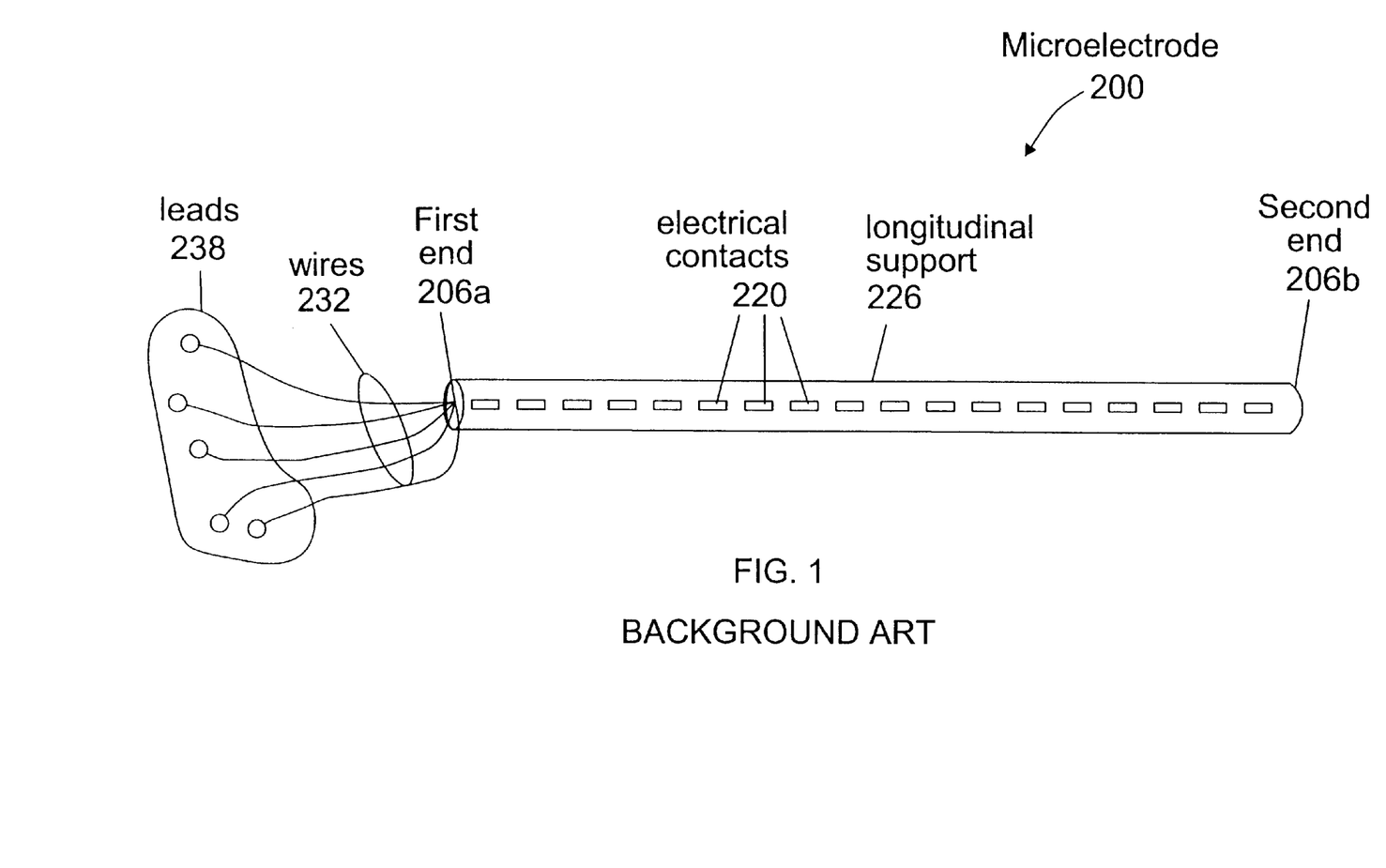
FIG. 1 is a diagram of a microelectrode that can be implanted in a patient's brain to sense electrical action potentials.

Brain mapping is typically carried out with a penetrating microelectrode, such as the one shown in FIG. 1. The microelectrode is inserted into a patient's brain to sense electrical action potentials. The microelectrode includes a longitudinal support 226 having a first end 206a and a second end 206b. The microelectrode also includes a plurality of electrical contacts 220 formed along the longitudinal support 226 of the microelectrode. One or more wires 232, connect the plurality of electrical contacts 220 to corresponding leads 238. The electrical leads 238 are then connected to a device which is capable of sensing a voltage generated adjacent the electrical contacts 220, or of applying a voltage to the contacts 220.

Figure 2:
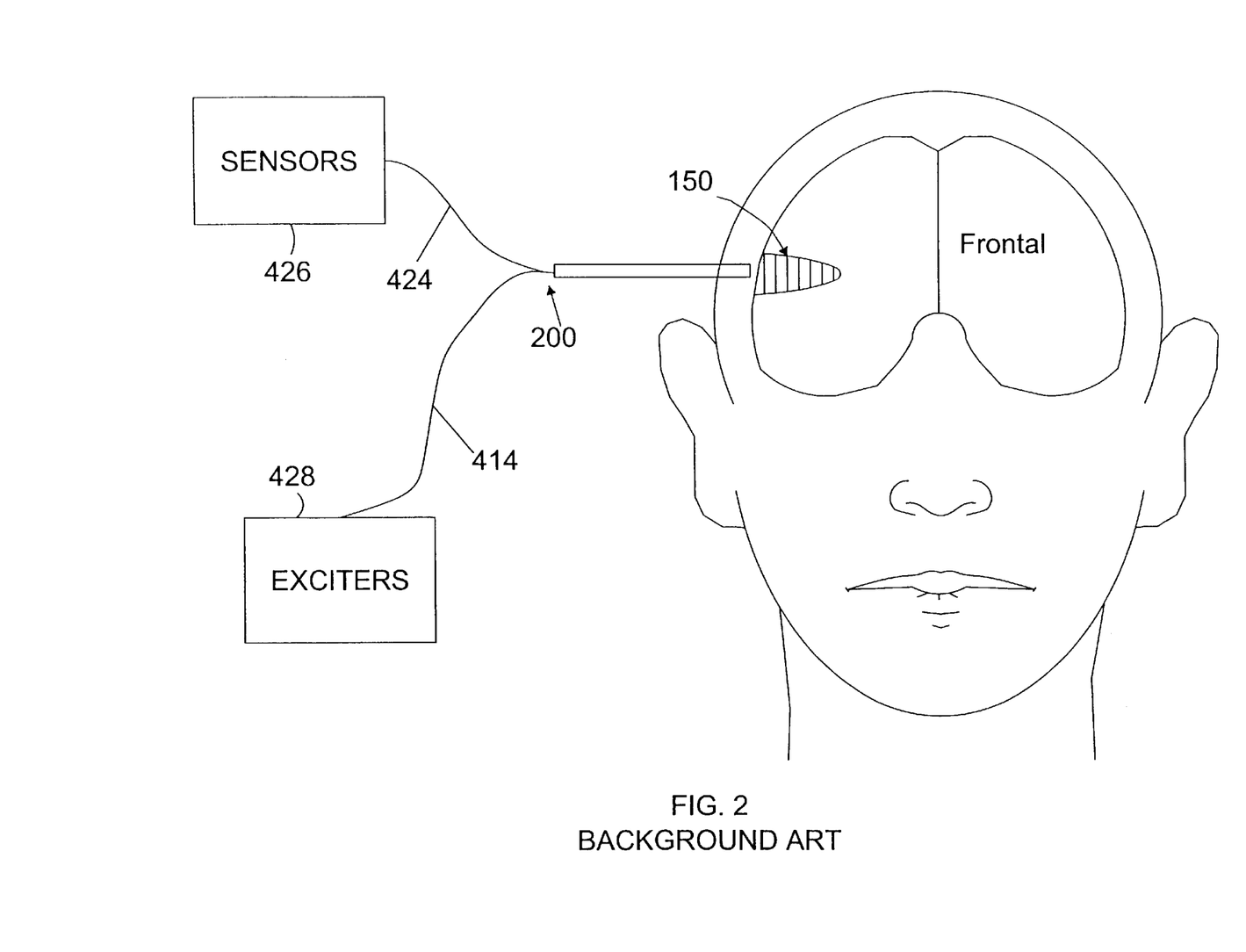
FIG. 2 is a diagram showing how a microelectrode can be inserted into a patient's brain.

To map a portion of a patient's brain, a microelectrode like the one shown in FIG. 1 is inserted through a burr hole into a portion 150 of a patient's brain, as shown in FIG. 2. The electrical contacts 220 on the microelectrode 200 are connected to one or more sensors 426 via an electrical cable 424. If, for example, functions relating to movement of the patient's arm are being mapped, the patient is then instructed to move his arm in some manner and the electrical action potentials that are produced by the patient's brain are sensed by the sensors 426, via the electrical contacts 220 of the microelectrode 200. Typically, only certain ones of the electrical contacts 220 will sense an electrical action potential. This indicates that the portions of the patient's brain adjacent the electrical contacts 220 sensing electrical action potentials are responsible for the particular movement of the patient's arm. The patient can then be instructed to move his arm in a different manner, and the electrical action potentials generated by this movement are also sensed by the microelectrode 200. In this manner, a neurosurgeon can determine exactly which portions of the patient's brain are responsible for particular types of arm movements.

At this point, the neurosurgeon could selectively excite certain electrical contacts 220 of the microelectrode 200 via exciters 428 connected to the microelectrode via a cable 414. It is sometimes possible for electrical excitation of selected portions of the patient's brain to reproduce particular types of arm movements.

A similar process can be followed to determine which portions of a patient's brain are responsible for processing certain frequency sounds. The patient's brain can then be electrically excited to cause the patient to "hear" certain sounds. Likewise, this process can be used to determine which portions of a patient's brain are responsible for processing sensory inputs from other sensory organs such as the eyes, the nose, or from touch receptors.

Figure 3:
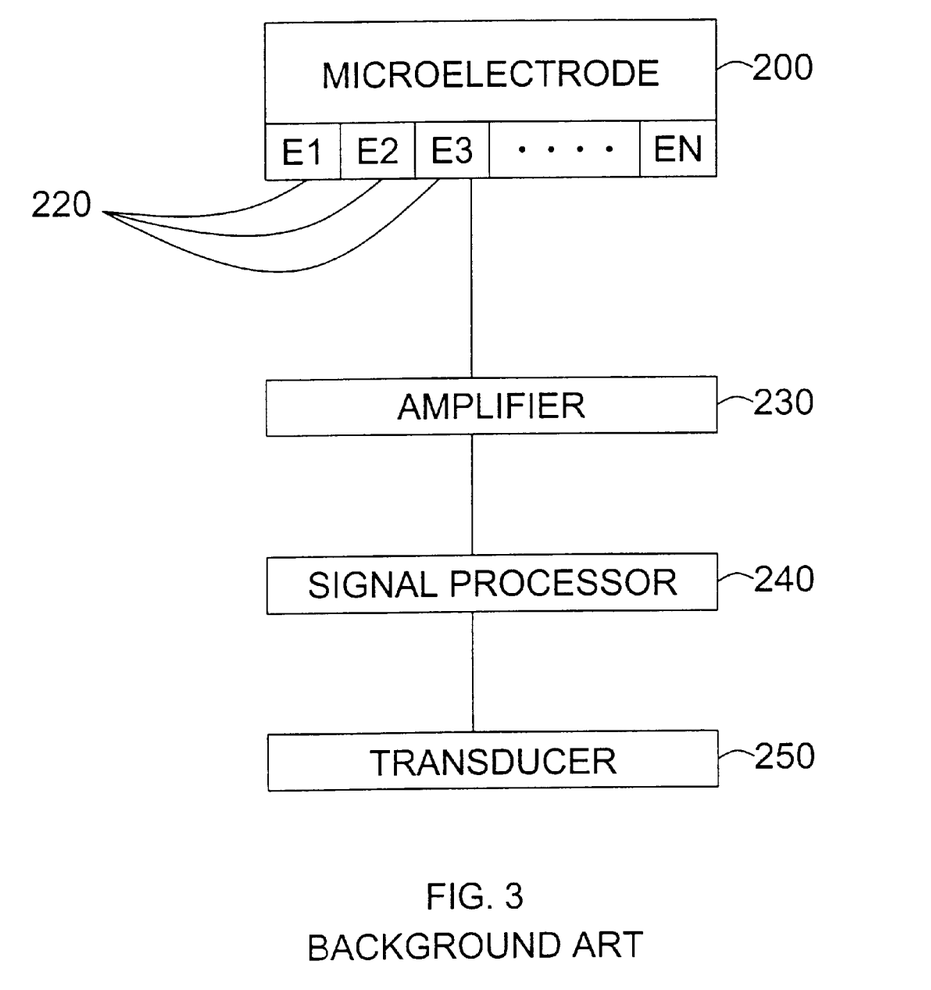
FIG. 3 is a block diagram of a known system for sensing electrical action potentials in a patient's brain.

FIG. 3 shows a typical system used to help map a patient's brain. The device includes a microelectrode 200, such as the one shown in FIG. 1, an amplifier 230, a signal processor 240, and a transducer 250. Individual electrical contacts 220 of the microelectrode 200 are connected to the amplifier 230, which amplifies any electrical action potentials generated in the patient's brain adjacent the electrical contacts 220. The amplified signals are then fed to a signal processor 240, which processes the amplified signals to determine whether the amplitude of the signals rises above a certain threshold level. When the amplitude of a sensed electrical action potential exceeds a predetermined threshold, the signal processor causes a transducer 250 to generate a user recognizable signal, such as an audible tone or the illumination of a lamp. Such a system is commonly known as an amplitude threshold discriminator.

Figure 4:
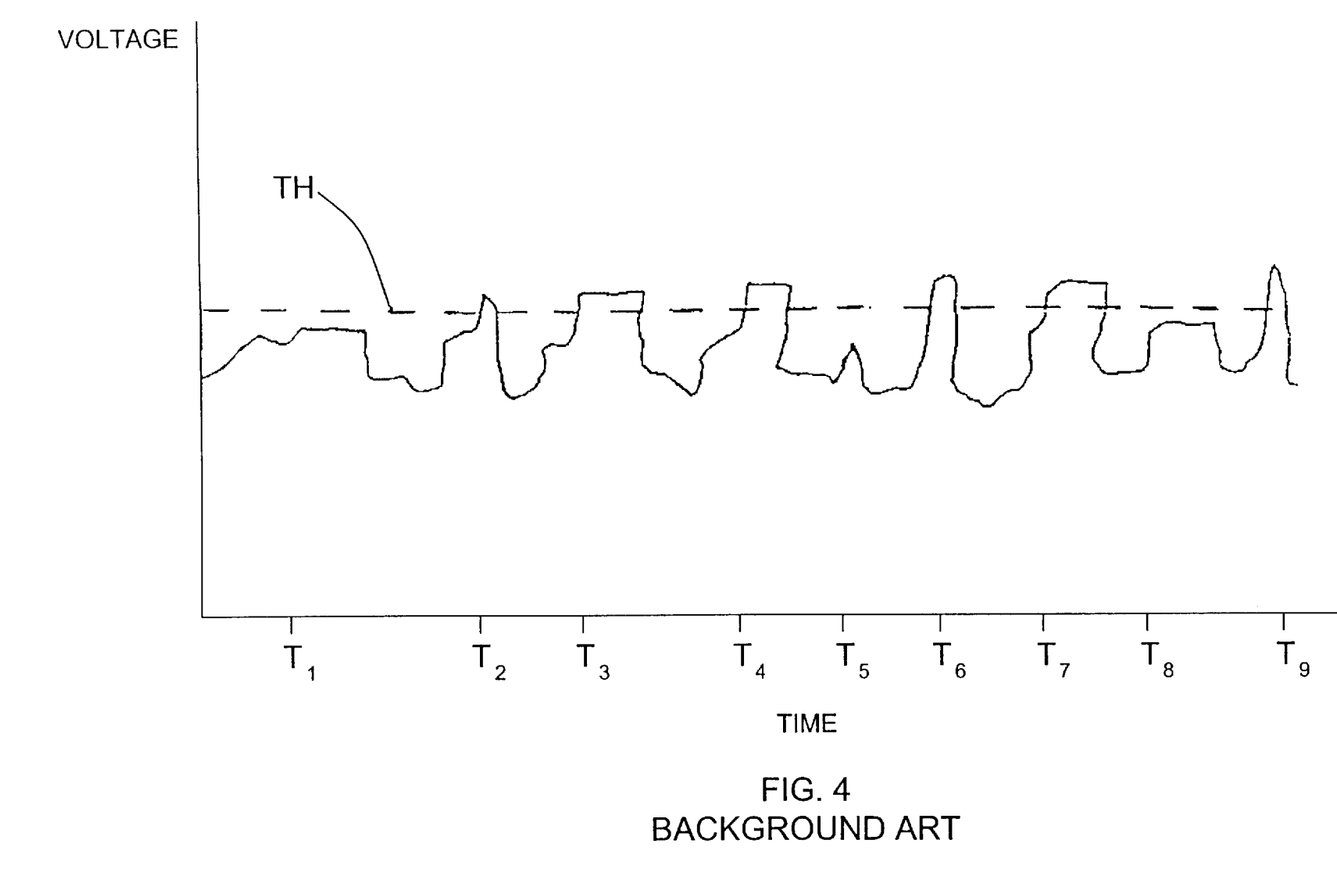
FIG. 4 is a diagram of sensed electrical action potentials over time.

FIG. 4 shows a plot of sensed electrical action potential voltage at a particular electrical contact 220 of a microelectrode 200 over time. The dashed line TH indicates a threshold electrical voltage. If a system like the one shown in FIG. 3 is used to sense the electrical action potential voltages shown in FIG. 4, whenever the voltage of the electrical action potential exceeds the threshold voltage TH, the transducer 250 of the system would output a user recognizable signal. For instance, at times T1, T5 and T8, the sensed electrical action potential voltage does not exceed the threshold voltage, and no user recognizable signal would be output. However, at times T2–T4, T6, T7 and T9, the sensed electrical action potential voltage exceeds the threshold voltage, and the transducer 250 of the system would output a user recognizable signal.

The prior art system described above cannot always accurately map a patient's brain because simply determining whether the voltage of an electrical action potential exceeds a threshold voltage does not provide enough information about the electrical activity occurring in the brain to accurately map the brain. Although an amplitude threshold discriminator, as described above, can eliminate some background noise, the system provides poor resolution and is incapable of accurately determining that a portion of a patient's brain is responsible for a certain activity if the electrical action potential associated with that activity does not exceed the threshold voltage.

SUMMARY OF THE INVENTION

The present invention is an apparatus and method for analyzing electrical action potentials in a patient's brain based on the waveforms of the sensed electrical action potentials. In a system or method embodying the invention, the waveforms of sensed electrical action potentials in the patient's brain are compared to one or more predetermined waveforms to determine whether the sensed electrical action potentials match or are substantially similar to the predetermined waveforms. An apparatus or method embodying the invention allows a neurosurgeon to determine whether a particular electrical action potential corresponds to a motor activity or sensory function with greater accuracy and precision. Thus, apparatus and methods embodying the invention allow a neurosurgeon to better map different portions of a patient's brain.

Additional advantages, objects, and features of the invention will be set forth in part in the description which follows, and in part will become apparent to those having ordinary skill in the art upon examination of the following, or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numbers refer to like elements, and wherein.

DETAILED DESCRIPTION OF PREFERRED EMBODIMENTS

Figure 6A:
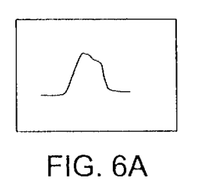
FIGS. 6A, 6B, 6C, 6D and 6E illustrate different waveforms of electrical action potentials that may be generated in a patient's brain.
Figure 6B:
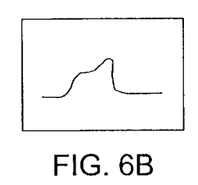
Figure 6C:
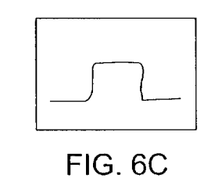
Figure 6D:
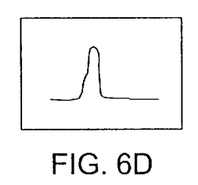
Figure 6E:
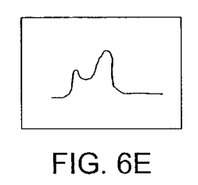
Figure 7:
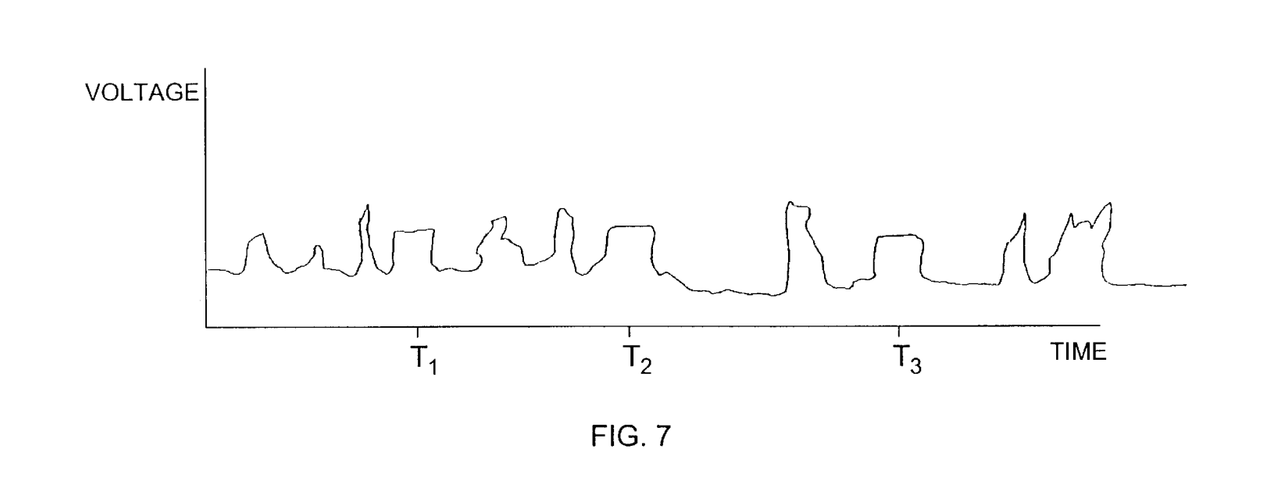
FIG. 7 illustrates a series of sensed electrical action potentials over time.

The inventor of the present invention has discovered that examining the waveforms of electrical action potentials generated in a patient's brain can allow a neurosurgeon to more accurately map a patient's brain. FIG. 6A shows a particular electrical action potential waveform that may be generated when a patient performs a certain motor activity or processes a particular sensory input. The waveform of FIG. 6A is different from the waveform of FIG. 6B, which may correspond to a different motor activity or sensory input. FIGS. 6C, 6D and 6E show other electrical action potential waveforms that may be generated by a patient's brain to perform other functions. As can be seen from examining these figures, different waveforms have different voltage amplitudes and different durations.

If a prior art amplitude threshold discriminator were used to sense these waveforms, and the threshold voltage was set slightly larger than the amplitude of the waveform shown in FIG. 6C, only the waveforms shown in FIGS. 6D and 6E would cause the system to output a signal. This means the prior art system would completely ignore electrical action potentials having the waveforms shown in FIGS. 6A, 6B and 6C. For this reason, the prior art system would fail to recognize certain electrical action potentials generated in the patient's brain that correspond to certain functions.

Figure 5:
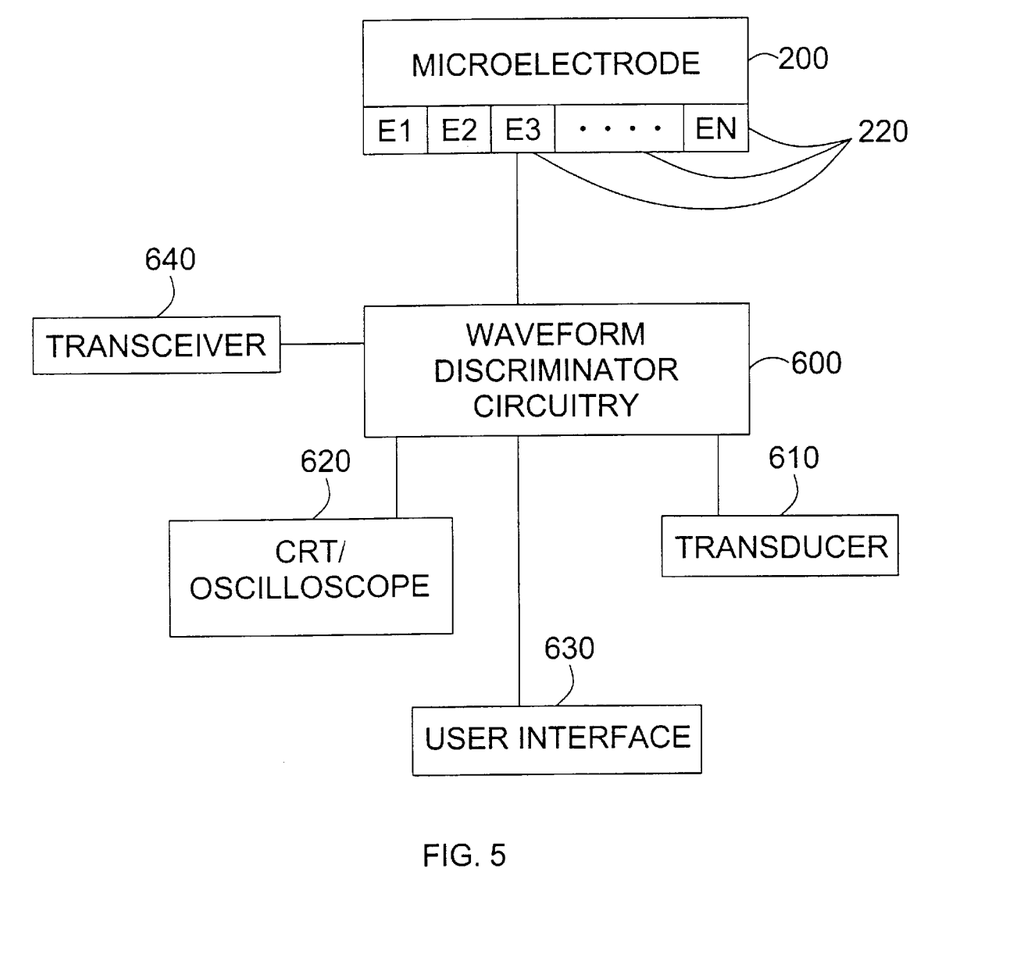
FIG. 5 is a block diagram of a system embodying the present invention.

A system embodying the present invention, as shown in FIG. 5, is capable of comparing the waveforms of sensed electrical action potentials to predetermined waveforms. This system includes a microelectrode 200, waveform discriminator circuitry 600, a transducer 610 and a user interface 630. The microelectrode 200 may include a plurality of electrical contacts 220 represented by the symbols E1, E2, E3–EN. The microelectrode 200 can be substantially similar to the microelectrode shown in FIG. 1, which is used with known systems for mapping a patient's brain.

The user interface 230 is used to select one or more waveforms to which sensed electrical action potentials will be compared. The user interface 630 may include one or more buttons for selecting predetermined waveforms like the ones shown in FIGS. 6A–6E. The user interface 630 may also include a display screen for displaying one or more predetermined waveforms so that a user can easily select a particular waveform. Alternately, the user interface 630 might include means for recording and/or displaying electrical action potentials generated by a patient's brain. This would allow a surgeon to select one or more waveforms previously produced by the patient's brain for comparison to waveforms of subsequently sensed electrical action potentials.

Figure 10:
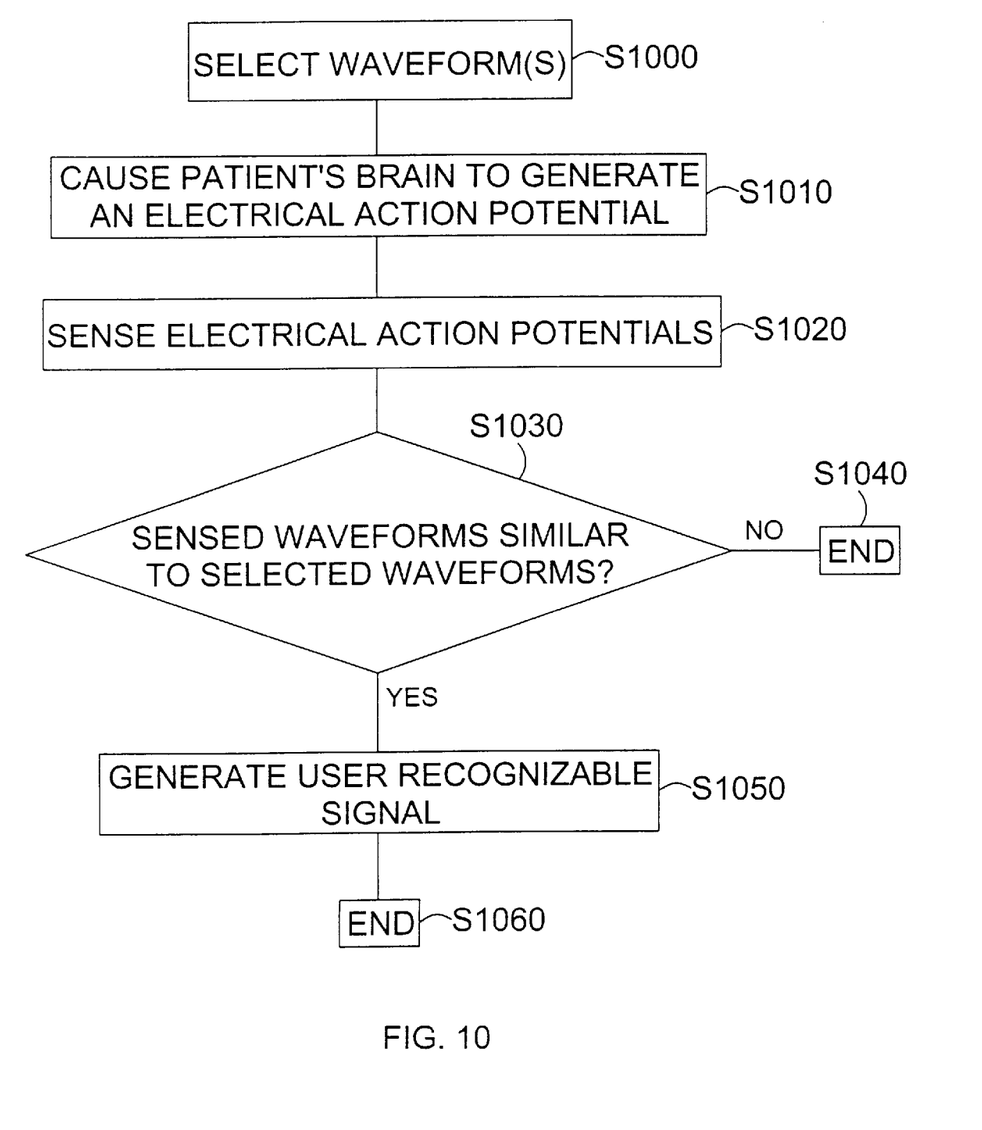
FIG. 10 is a flowchart showing steps of a method embodying the invention.

A method embodying the invention is shown in FIG. 10. In step S1000, a user would first select one or more predetermined waveforms to be compared to the waveforms of sensed electrical action potentials in a patient's brain. Next, in step S1010, the user would cause a patient's brain to perform a certain function, such as causing the patient to move a limb or causing the patient to listen to a particular frequency tone. In step S1020, an electrical action potential produced in the patient's brain during this activity would be sensed by a microelectrode, which communicates the electrical action potential to waveform discrimination circuitry. In step S1030, the waveform discrimination circuitry would compare the waveform of the sensed electrical action potential to the selected waveforms to determine whether the sensed waveform is substantially similar to the selected waveform. If the sensed waveform is substantially similar, in step S1050 the system would output a user recognizable signal. For instance, the user recognizable signal could be an audible tone or illumination of a lamp. If the sensed waveform is not substantially similar to the selected waveform, no action would be taken.

Figure 11:
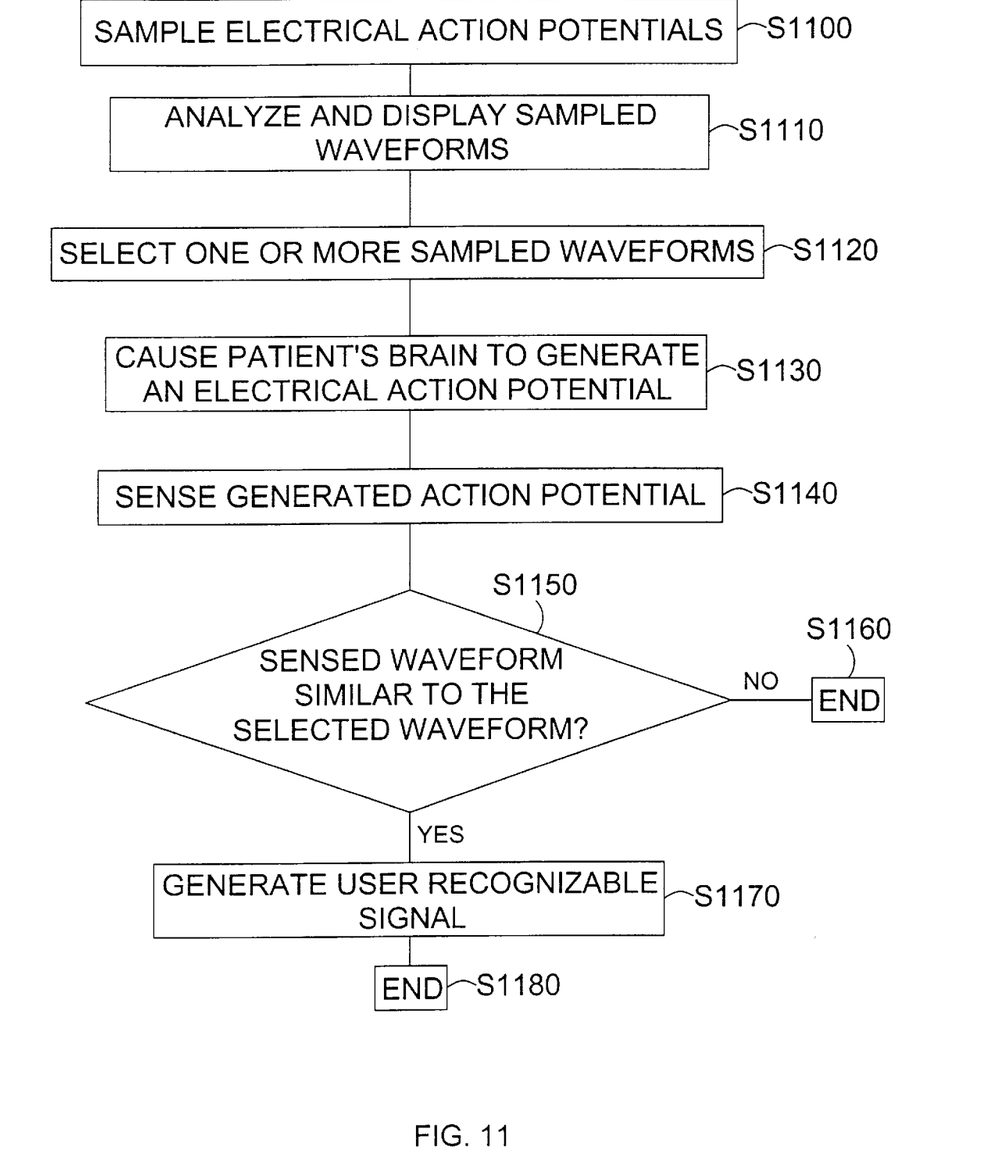
FIG. 11 is a flowchart showing steps of another method embodying the invention.

Another method embodying the invention, is shown in FIG. 11. In step S1100, electrical action potentials from the patient's brain are sampled. In step S1110, the sensed waveforms are analyzed to identify particular waveforms and the identified waveforms are displayed to the user. The identified waveforms could be presented to the user with the user interface 630, or on a separate CRT/Oscilloscope 620.

In step S1120, the user would select one or more of the identified waveforms. The remaining steps of the method, steps S1130–S1180, are identical to steps S1010–S1060, which are described with reference to FIG. 10.

When a microelectrode used with an apparatus or method embodying the invention includes a plurality of electrical contacts 220, the system can selectively monitor an individual electrical contact 220 to determine whether an electrical action potential generated adjacent the electrical contact has a waveform similar to a pre-selected waveform. In this manner, a neurosurgeon is able to identify individual locations in the patient's brain responsible for particular functions or activity.

Figure 8:
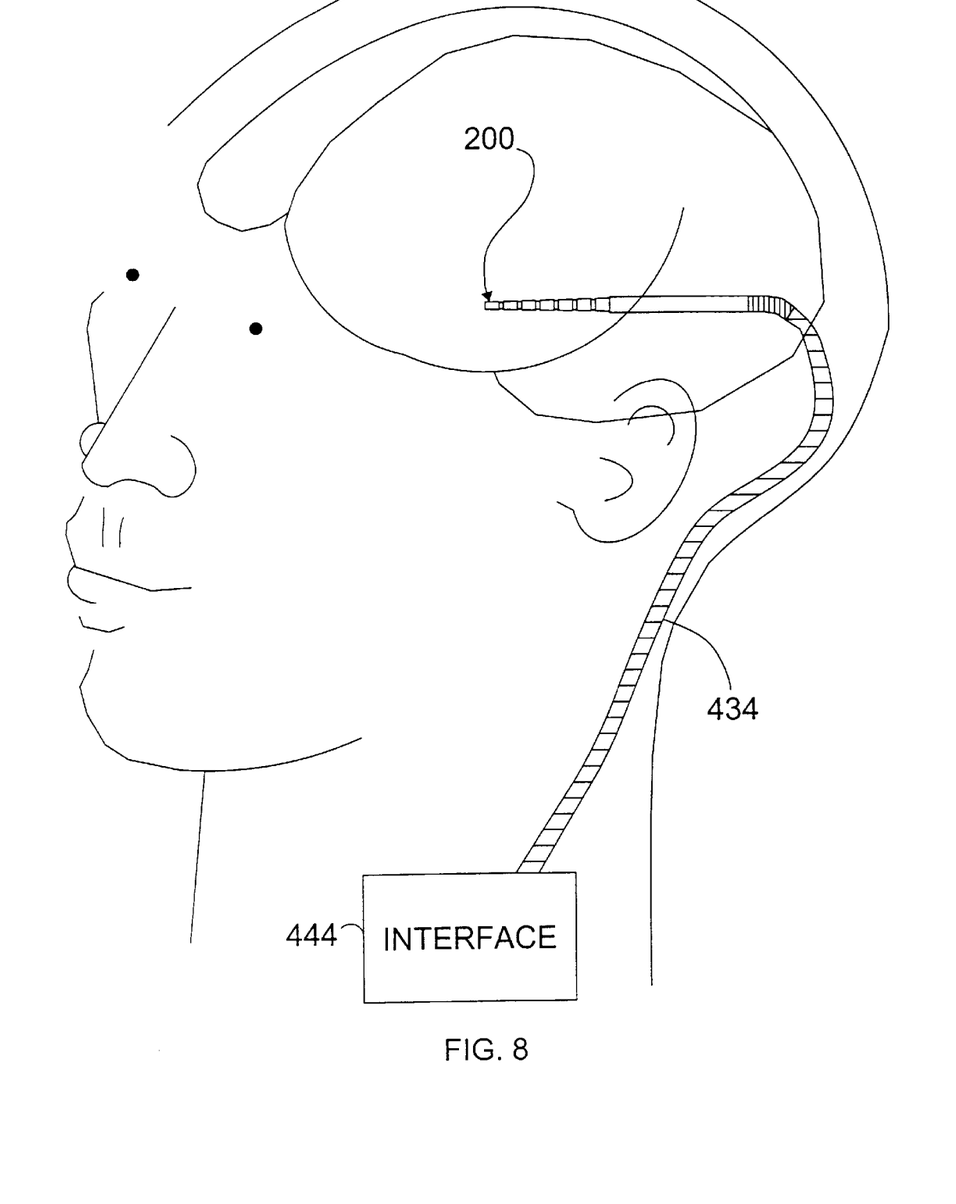
FIG. 8 illustrates a microelectrode and interface that can be utilized with a system embodying the present invention.

As shown in FIG. 8, an apparatus embodying the invention may include a microelectrode 200 connected to a user interface 444 via an electrical cable 434. In this system, the microelectrode 200, cable 434 and interface 444 may be implanted in the patient's brain, scalp and neck during a surgical procedure. After the patient has recovered from the surgical procedure, the interface could be connected to waveform discriminator circuitry of a system embodying the This allows the brain mapping tong. This allows the brain mapping to occur outside the operating room, which reduces costs and simplifies the procedure.

Figures 9A, 9B:
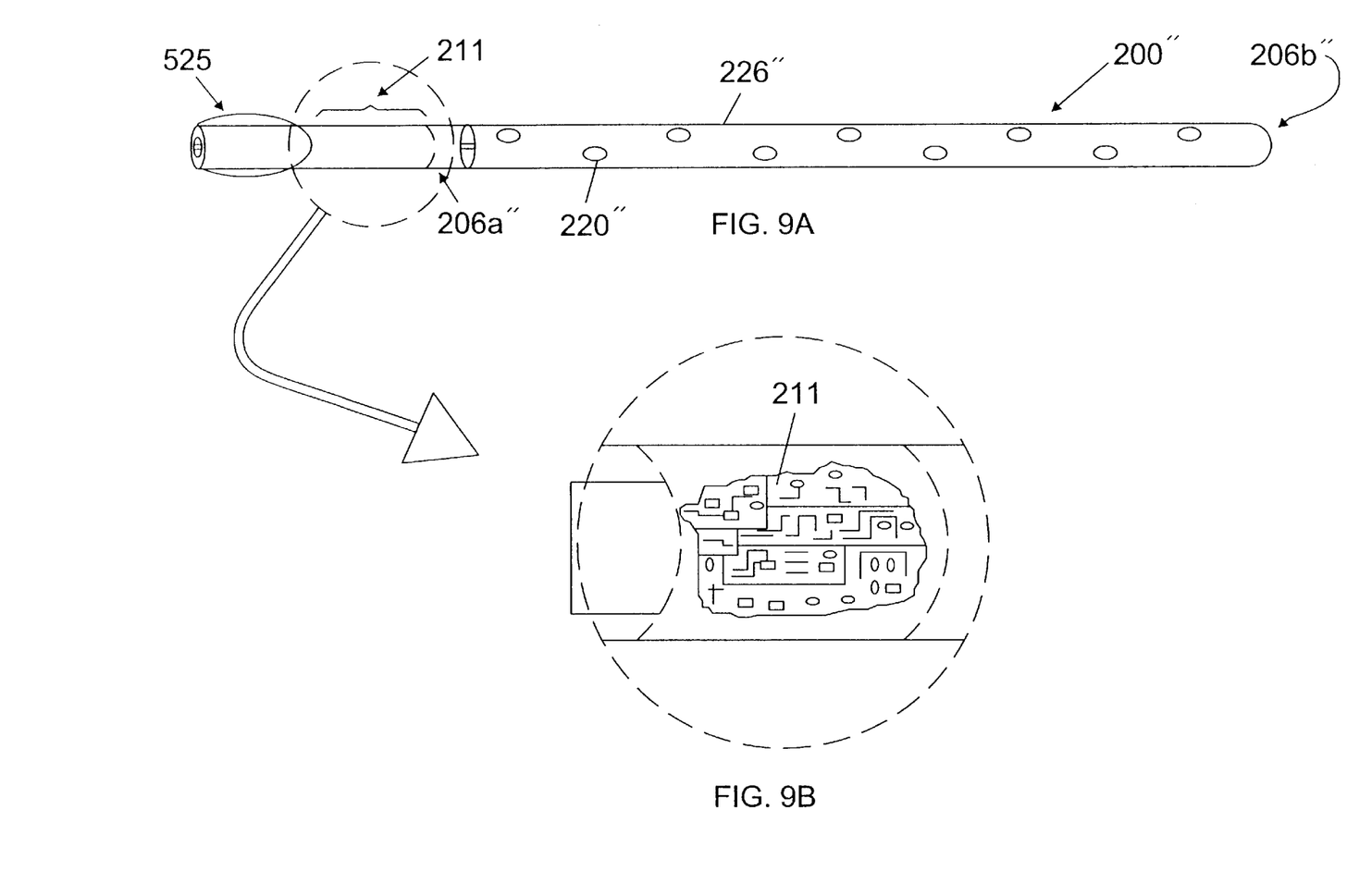
FIG. 9A illustrates another microelectrode that can be used with a system embodying the invention.
FIG. 9B is an enlarged view of a portion of the microelectrode shown in FIG. 9A.

In another embodiment of the invention, the microelectrode 200', as shown in FIG. 9A, may include transceiver circuitry 211, as shown in FIG. 9B. In a system including the microelectrode shown in FIGS. 9A and 9B, the microelectrode 200 can be implanted in a patient's brain during a surgical procedure. After the surgical procedure is complete and the patient has recovered, brain mapping can be performed using waveform discriminator circuitry that is connected to a transceiver capable of communicating with the microelectrode 200' shown in FIGS. 9A and 9B. For instance the transceiver circuitry 211 would be used to communicate with a transceiver 640 connected to the waveform discriminator circuitry 600 of the system, as shown in FIG. 5. This eliminates the need for electrical connections that protrude from the patient's head or neck and further simplifies the brain mapping procedure.

The foregoing embodiments are merely exemplary and are not intended to limit the scope of the appended claims. Many alternatives, modifications and variations will be apparent to those skilled in the art.

What is claimed is:

1. A method of analyzing electrical activity in a patient's brain, comprising the steps of:
    sensing an electrical action potential with a sensor located in or on the patient's brain;
    comparing the sensed electrical action potential with a predetermined waveform; and
    determining whether a waveform of the sensed electrical action potential is substantially similar to the predetermined waveform.

2. The method of claim 1, further comprising the step of generating a user recognizable signal when it is determined that the waveform of the sensed electrical action potential is substantially similar to the predetermined waveform.

3. The method of claim 1, further comprising the step of selecting a predetermined waveform from among a plurality of predetermined waveforms, and wherein the comparing step comprises comparing the sensed electrical action potential to the selected predetermined waveform.

4. The method of claim 1, wherein the step of sensing an electrical action potential comprises sensing an electrical action potential with a microelectrode inserted in the patient's brain.

5. The method of claim 1, further comprising the step of inserting a microelectrode in the patient's brain.

6. The method of claim 5, wherein the step of sensing an electrical action potential comprises sensing an electrical action potential with the microelectrode.

7. The method of claim 5, wherein the microelectrode includes a plurality of electrical sensors, and wherein the step of sensing an electrical action potential comprises sensing an electrical action potential with a selected sensor of the microelectrode.

8. The method of claim 5, wherein the microelectrode includes a plurality of electrical sensors, and wherein the step of sensing an electrical action potential comprises sensing an electrical action potential with a selected plurality of the sensors of the microelectrode.

9. A method of mapping a portion of patient's brain, comprising the steps of:
    inducing the patient's brain to generate an electrical action potential;
    sensing the generated electrical action potential with a sensor located in or on the patient's brain;
    comparing a waveform of the sensed electrical action potential to at least one predetermined waveform; and
    determining whether the waveform of the sensed electrical action potential is similar to the at least one predetermined waveform.

10. The method of claim 9, wherein the step of sensing the generated electrical action potential occurs in a portion of the patient's brain responsible for processing optical activity, and wherein the step of inducing the patient's brain to generate an electrical action potential comprises causing the patient to look at something.

11. The method of claim 9, wherein the step of sensing the generated electrical action potential occurs in a portion of the patient's brain responsible for processing sounds, and wherein the step of inducing the patient's brain to generate an electrical action potential comprises causing the patient to listen to a sound.

12. The method of claim 9, wherein the step of sensing the generated electrical action potential occurs in a portion of the patient's brain responsible for processing olfactory activity, and wherein the step of inducing the patient's brain to generate an electrical action potential comprises causing the patient to smell something.

13. The method of claim 9, wherein the step of sensing the generated electrical action potential occurs in a portion of the patient's brain responsible for processing tactile sensory activity, and wherein the step of inducing the patient's brain to generate an electrical action potential comprises causing the patient to feel something.

14. The method of claim 9, wherein the step of sensing the generated electrical action potential occurs in a portion of the patient's brain responsible for processing motor activity, and wherein the step of inducing the patient's brain to generate an electrical action potential comprises causing the patient to move a portion of his body.

15. The method of claim 9, wherein the step of sensing an electrical action potential in the patient's brain comprises sensing an electrical action potential at a selected location in the patient's brain, and further comprising the step of determining that the selected location of the patient's brain is responsible for processing a type of activity that induced the electrical action potential when it is determined that the waveform of the sensed electrical action potential is similar to the at least one predetermined waveform.

16. The method of claim 9, further comprising the steps of:

inserting a microelectrode in a selected location in the patient's brain, wherein the step of sensing an electrical action potential comprises sensing an electrical action potential with the microelectrode; and determining that the selected location of the patient's brain is responsible for processing a type of activity that induced the patient's brain to generate the electrical action potential when it is determined that the waveform of the electrical action potential is similar to the at least one predetermined waveform.

17. The method of claim 16, wherein the step of inserting a microelectrode in the patient's brain comprises inserting a microelectrode having a plurality of sensors, wherein the step of sensing an electrical action potential comprises sensing an electrical action potential with a selected sensor at a predetermined position on the microelectrode, and wherein the determining step comprises determining that a portion of the patient's brain adjacent the selected sensor processes the type of activity when the waveform of the electrical action potential is similar to the at least one predetermined waveform.

18. A device for analyzing electrical activity in a patient's brain, comprising:

means for sensing an electrical action potential in the patient's brain, wherein the sensing means is configured to be located in or on the patient's brain;

means for comparing a waveform of a sensed electrical action potential with a predetermined waveform; and means for determining whether the waveform of the sensed electrical action potential is substantially similar to the predetermined waveform.

19. The device of claim 18, further comprising means for generating a user recognizable signal when it is determined that the waveform of the sensed electrical action potential is substantially similar to the predetermined waveform.

20. The device of claim 18, further comprising means for selecting a predetermined waveform from among a plurality of predetermined waveforms.

21. The device of claim 18, wherein the means for sensing an electrical action potential comprises means for sensing an electrical action potential at a selected portion of the patient's brain.

22. A device for analyzing electrical activity in a patient's brain, comprising:

a microelectrode, configured to be located in or on a patient's brain, and having at least one sensor for sensing an electrical action potential in the patient's brain;

a waveform discriminator connected to the microelectrode for determining whether a sensed electrical action potential has a waveform that is similar to at least one selected waveform; and a transducer for generating a user recognizable signal when the waveform discriminator determines that the waveform of the sensed electrical action potential is similar to the at least one selected waveform.

23. The device of claim 22, wherein the electrode comprises a plurality of sensors for sensing electrical action potentials at a corresponding plurality of locations in the patient's brain.

24. The device of claim 22, wherein the waveform discriminator includes a display screen for displaying a waveform of a sensed electrical action potential.

25. The device of claim 24, wherein the waveform discriminator is capable of displaying a plurality of waveforms on the display screen, and wherein the waveform discriminator includes means for selecting at least one selected waveform from among a plurality of displayed waveforms.

26. The device of claim 22, wherein the waveform discriminator comprises selection means for selecting the at least one selected waveform from among a plurality of waveforms.

27. The device of claim 26, wherein the selection means allow a user to select the at least one selected waveform from among a plurality of predetermined waveforms.

28. The device of claim 26, wherein the device is capable of recording a plurality of sensed electrical action potentials, wherein the waveform discriminator is capable of identifying a plurality of waveforms corresponding to the recorded electrical action potentials, and wherein the selection means allows a user to select the at least one selected waveform from among the identified waveforms of the recorded electrical action potentials.

29. The device of claim 22, wherein the transducer comprises one of a speaker, a lamp, and a display screen.

30. A waveform discriminator for determining a waveform of an electrical action potential sensed within or on a patient's brain, comprising:

a selection device for selecting at least one waveform;

a detector for detecting a waveform of an electrical action potential sensed within or on a patient's brain; and a comparator for determining whether the detected waveform of the electrical action potential is similar to at least one selected waveform.

31. The waveform discriminator of claim 30, wherein the selection device allows a user to select the at least one waveform from among a plurality of predetermined waveforms.

32. The waveform discriminator of claim 30, wherein the detector detects waveforms of a plurality of electrical action potentials, and wherein the selection device allows a user to select the at least one waveform from among the detected waveforms of the plurality of electrical action potentials.

33. The waveform discriminator of claim 30, further comprising an interface for connecting the detector to a microelectrode that is insertable in a patient's brain.

34. The waveform discriminator of claim 33, wherein the interface comprises at least one electrically conductive wire.

35. The waveform discriminator of claim 33, wherein the interface comprises a receiver that receives electromagnetic signals transmitted by the microelectrode.

36. The waveform discriminator of claim 33, wherein the interface comprises a transceiver that communicates with a transceiver of the microelectrode via electromagnetic radiation.

37. The waveform discriminator of claim 30, further comprising a display screen for displaying waveforms.

38. A method of determining whether a waveform of an electrical action potential generated in a patient's brain is similar to a selected waveform, comprising the steps of:

selecting at least one waveform from among a plurality of waveforms;

comparing a waveform of an electrical action potential generated in a patient's brain and sensed with a sensor located in or on the brain, to the selected at least one waveform; and determining whether the waveform of the electrical action potential is similar to the selected at least one waveform.

39. The method of claim 38, further comprising the step of detecting a waveform of the electrical action potential using a sensor located in or on the patient's brain.

40. The method of claim 38, wherein the step of selecting at least one waveform comprises selecting at least one waveform from among a plurality of predetermined waveforms.

41. The method of claim 38, wherein the step of selecting at least one waveform comprises selecting at least one waveform from among a plurality of waveforms of a plurality of electrical action potentials generated in the patient's brain.

42. The method of claim 38, further comprising the step of generating a user recognizable signal when it is determined that the waveform of the electrical action potential is similar to the at least one selected waveform.

* * * * *